United States Patent
Tanaka et al.

(10) Patent No.: US 10,094,816 B2
(45) Date of Patent: Oct. 9, 2018

(54) METHOD OF EVALUATING WETTING CHARACTERISTIC OF OBJECT

(71) Applicant: TOKYO WOMEN'S MEDICAL UNIVERSITY, Shinjuku-ku (JP)

(72) Inventors: Nobuyuki Tanaka, Shinjuku-ku (JP); Ryohei Uchida, Nabari (JP); Makoto Kondo, Shinjuku-ku (JP); Masayuki Yamato, Shinjuku-ku (JP); Teruo Okano, Shinjuku-ku (JP); Makoto Kaneko, Suita (JP)

(73) Assignee: TOKYO WOMEN'S MEDICAL UNIVERSITY, Shinjuku-ku (JP)

( * ) Notice: Subject to any disclaimer, the term of this patent is extended or adjusted under 35 U.S.C. 154(b) by 593 days.

(21) Appl. No.: 14/391,614

(22) PCT Filed: May 24, 2013

(86) PCT No.: PCT/JP2013/064510
§ 371 (c)(1),
(2) Date: Oct. 9, 2014

(87) PCT Pub. No.: WO2013/176264
PCT Pub. Date: Nov. 28, 2013

(65) Prior Publication Data
US 2015/0072370 A1 Mar. 12, 2015

Related U.S. Application Data

(60) Provisional application No. 61/651,875, filed on May 25, 2012.

(51) Int. Cl.
G01N 33/483 (2006.01)
G01N 13/00 (2006.01)
G01N 13/02 (2006.01)

(52) U.S. Cl.
CPC ......... *G01N 33/4833* (2013.01); *G01N 13/00* (2013.01); *G01N 13/02* (2013.01); *G01N 2013/0208* (2013.01)

(58) Field of Classification Search
None
See application file for complete search history.

(56) References Cited

PUBLICATIONS

Lee et al. 1993. A wettability gradient as a tool to study protein adsorption and cell adhesion on polymer surfaces. Journal of biomaterials science. Polymer edition, vol. 4, No. 5, pp. 467-481.*
Extended Search Report dated Dec. 7, 2015 in European Patent Application No. 13794220.7.
Ryohei Uchida, et al., "Cell Sheet Stiffness Sensing without taking out from culture liquid", $32^{nd}$ Annual International Conference of the IEEE Engineering in Medicine and Biology Society, (EMBS 2010), 2010, pp. 827-830.
Nobuyuki Tanaka, et al., "Noncontact Active Sensing for Viscoelastic Parameters of Tissue With Couplinig Effect", IEEE Transactions on Biomedical Engineering, IEEE Service Center, vol. 58, No. 3, Mar. 2011 , pp. 509-520.
Nobuyuki Tanaka, et al., "Noncontact Evaluation of the Wetting Characteristic of a Cell Sheet in Culture Medium", Proceedings of 2012 IEEE International Conference on Mechatronics and Automation, pp. 986-991, (2012).
Elias Lazarides, et al., "Actin Antibody: The Specific Visualization of Actin Filaments in Non-Muscle Cells", Proceedings of the National Academy of Sciences, vol. 71, No. 6, pp. 2268-2272, (Jun. 1974).
International Search Report dated Jul. 2, 2013 in PCT/JP13/064510 Filed May 24, 2013.

* cited by examiner

*Primary Examiner* — Louise Humphrey
*Assistant Examiner* — Kailash C Srivastava
(74) *Attorney, Agent, or Firm* — Oblon, McClelland, Maier & Neustadt, L.L.P.

(57) ABSTRACT

Provided is a means for evaluating the wetting characteristic of an object such as a cell sheet and a culture dish in a non-contact fashion. The wetting characteristic of an object is evaluated by a method comprising the steps of: (1) removing a liquid by jetting a gas at a surface of the object covered with the liquid, (2) measuring a dimension of a region in which the liquid is removed after the completion of the gas jetting and (3) evaluating the wetting characteristic of the object using the measured dimension as an index.

8 Claims, 9 Drawing Sheets

Fig.4

Control

FBS (-)

air jet application

METHOD OF EVALUATING WETTING CHARACTERISTIC OF OBJECT

CROSS REFERENCE TO RELATED APPLICATIONS

The present application is a 35 U.S.C. § 371 national stage patent application of International patent application PCT/JP2013/064510, filed on May 24, 2013, and claims the benefit of the filing date of U.S. Provisional application No. 61/651,875, filed on May 25, 2012.

TECHNICAL FILED

The present invention relates to a method of evaluating wetting characteristic (ease of wetting) of a surface of an object such as a cell sheet and a culture dish, and a system which can be used for the method.

BACKGROUND ART

Mucosal epithelium is widely distributed over tissues in cornea, gastrointestinal tract and the like. Mucosal epithelium maintains the moisture at a tissue surface, and serves to protect the body homeostasis against change in the external environment. However, depending on various factors, the wetting characteristic of a tissue surface may decrease, resulting in diseases such as dry eye and gastrointestinal tract ulcer.

In recent years, as a branch of regenerative medicine, a therapy has gathered attention in which a cell sheet obtained by plane-culturing mucosal epithelial cells is transplanted in living tissues which have lost mucosal epithelium. For example, a sheet of human mucosal epithelial cells is already in use for cornea transplantation.

However, the manufacture of a cell sheet generally requires complicated culture processes, and is susceptible to cell conditions and culture environment. Accordingly, a technology for evaluating the quality of a manufactured cell sheet is demanded. In particular, for a sheet of mucosal epithelial cells, wetting characteristic serves as an important measure of whether the cell sheet is capable of covering affected tissues.

The wetting characteristic of an object may be evaluated, for example, by the contact angle between a liquid and a surface of the object (the contact angle method). In other words, the larger is the value of the contact angle, the lower is the wetting characteristic, and the smaller is the value of the contact angle, the higher is the wetting characteristic. In the contact angle method, a droplet may be formed on a surface of an object for which wetting characteristic is to be evaluated to measure the contact angle. Alternatively, in the contact angle method, a surface of an object for which wetting characteristic is to be evaluated may be immersed into a liquid with face-down, and air and the like may be supplied from below to allow the air to adhere on the surface. Then the contact angle may be measured.

The wetting characteristic of a planar object such as a sheet and a plate may also be evaluated based on the force required to pull the object out of a liquid after the object is suspended in the liquid (the Wilhelmy plate method).

Meanwhile, in the field of cell biology, fluorescence microscopy is used for detecting specific intracellular proteins (Nonpatent Literature 1).

CITATION LIST

Nonpatent Literature

Non-patent Literature 1: E. Lazarides and K. Weber, *Proceedings of the National Academy of Sciences*, Vol. 71, 1974, pp. 2268-2272.

SUMMARY OF INVENTION

Technical Problem

Mainly, the following three problems have been considered herein for evaluating properties of a cell sheet during culture:

(1) A cell sheet during culture is unable to be separated from a culture dish.
(2) A cell sheet should be free from a contamination.
(3) A cell sheet is fragile due to the thin thickness.

Therefore, it is difficult to apply Wilhelmy plate method to a cell sheet. Moreover, when the contact angle method was applied to a cell sheet under water, the air supplied from below the cell sheet did not rest on a surface of the cell sheet, clearly indicating that the contact angle could not be measured.

A method of detecting a specific protein by fluorescence microscopy can also be applied to the analysis of functions of a cell sheet. However, it is difficult to use such a method in evaluating the quality of a manufactured cell sheet because dyes generally have cytotoxicity and a cell sheet stained with a dye can not be used for medical purposes.

Accordingly, an object of the present invention is to provide a method of evaluating the wetting characteristic of an object such as a cell sheet and a culture dish in a non-contact fashion.

Solution to Problem

After conducting extensive studies to achieve the above object, the present inventors have found that the wetting characteristic of a cell sheet can be evaluated by jetting air at the cell sheet in a liquid medium to partly remove the liquid medium, and then measuring a dimension of a region in which the residual medium after the completion of air jetting remains removed. Then the present invention has been completed.

In other words, the present invention may be illustrated as follows.

[1] A method of evaluating the wetting characteristic of an object, the method comprising the steps of:
(1) removing a liquid by jetting a gas at a surface of the object covered with the liquid;
(2) measuring a dimension of a region in which the liquid is removed after the gas jetting; and
(3) evaluating the wetting characteristic of the object using the measured dimension as an index.
[2] The method according to [1], wherein the object is a sheet-like object.
[3] The method according to [2], wherein the sheet-like object is a cell sheet.
[4] The method according to any one of [1] to [3], wherein the liquid is a culture medium.
[5] The method according to any one of [1] to [4], wherein the gas is air.
[6] The method according to any one of [1] to [5], wherein the step (2) is performed by photographing the region in which the liquid is removed, and obtaining the dimension of the region in which the liquid is removed from the resulting photographed image.

[7] The method according to [1], wherein the object is a cell sheet,
the gas is air, and
the liquid is a culture medium.

[8] The method according to [1], wherein the object is a cell sheet,
the gas is air,
the liquid is a culture medium, and
the step (2) is performed by photographing the region in which the liquid is removed, and obtaining the dimension of the region in which the liquid is removed from the resulting photographed image.

[9] The method according to [1], wherein the object is a culture dish,
the gas is air, and
the liquid is a culture medium.

[10] The method according to [1], wherein the object is a culture dish,
the gas is air,
the liquid is a culture medium, and
the step (2) is performed by photographing the region in which the liquid is removed, and obtaining the dimension of the region in which the liquid is removed from the resulting photographed image.

[Item 11] The method of manufacturing an object, the method comprising the step of evaluating the wetting characteristic of the object by the method according to any one of [1] to [10].

[12] A system for evaluating the wetting characteristic of an object, comprising:
(1) a means for removing a liquid by jetting a gas at a surface of the object covered with the liquid; and
(2) a means for measuring a dimension of a region in which the liquid is removed.

[13] The system according to [12], further comprising (3) a means for evaluating the wetting characteristic of the object using the measured dimension as an index.

[14] The system according to [12] or [13], wherein the means (2) comprises an imaging unit for photographing the region in which the liquid is removed, and a dimension acquiring unit for obtaining the dimension of the region in which the liquid is removed from the resulting photographed image.

[15] The system according to any one of [12] to [14], which is used for performing the method according to any one of [1] to [11].

DESCRIPTION OF EMBODIMENTS

<1> Evaluation Method According to Present Invention

The evaluation method according to the present invention evaluate the wetting characteristic of an object.

There is no particular limitation for the object for which wetting characteristic is evaluated. In other words, for example, there is no particular limitation for types, properties, shapes and uses of the object. Shapes of the object include, for example, a sheet-like, a plate-like, a curved surface-like, a cylinder-like, a polyhedron-like, a container-like shapes and combinations thereof. The object may be, for example, a device or raw material for medical use, for therapeutic use, for experimental use, or for cell cultures.

Objects having a sheet-like shape (also referred to as sheet-like objects) include, for example, a cell sheet. A cell sheet may be manufactured from any types of cells. Specific examples of cell sources of cell sheets include embryonic stem cells (ES cells), induced pluripotent stem cells (iPS cells), mesenchymal stem cells, neural stem cells, hepatic stem cells, pancreatic stem cells, skin stem cells, oral mucosal epithelial cells, corneal limbus cells, periodontal ligament cells, fibrocytes, hepatic cells, pancreatic cells, chondrocytes, nasal mucosal cells and myoblasts. Cell sources may be those separated from living tissues, those obtained by culturing and/or differentiating cells separated from living tissues, or those obtained by modifying them with a technology such as genetic engineering. There is no particular limitation for organisms from which cells are derived, but may be appropriately selected depending on intended uses and the like. Organisms from which cells are derived include, for example, mammals. Specific examples of mammals include human, rat, mouse, guinea pig, marmoset, rabbit, canine, feline, sheep, swine and chimpanzee. When a cell sheet is used for treating human, cells from, for example, human, swine or chimpanzee are preferably used. For a cell source, only one type of cells may be used, or two or more types of cells may be used in combination.

A thickness of a sheet-like object may or may not be uniform. A thickness of a sheet-like object may be uniform throughout the sheet-like object, or may be uniform at a portion of the sheet-like object. A thickness of a sheet-like object may be uniform, for example, at least in a region where its surface is exposed by a gas jet. There is no particular limitation for a thickness of a sheet-like object, but, for example, it may be 0.01 µm or more, 0.1 µm or more, 1 µm or more, or 3 µm or more, and may be 5 mm or less, 1 mm or less, 500 µm or less, or 100 µm or less. Specifically, a thickness of a sheet-like object may be 20 µm. A thickness of a sheet-like object may fall in the ranges illustrated above throughout the sheet-like object, or may fall in the ranges illustrated above at a portion of the sheet-like object. A thickness of a sheet-like object may fall in the ranges illustrated above at least in a region where its surface is exposed by a gas jet.

Objects having a container-like shape (also referred to as container-like objects) include, for example, a culture dish. A culture dish can be used for cell culture, but it may also be employed for uses other than cell culture. A culture dish may be made of, for example, plastics or glass. A surface of a culture dish may have been subjected to coating treatment. Materials used for the coating treatment include, for example, collagen, extracellular matrix and a temperature responsive polymer. In other words, specific examples of culture dishes include those coated with a temperature responsive polymer (a temperature responsive culture dish). Further, a culture dish may have been subjected to various surface treatments. Surface treatments include oxygen plasma treatment.

The object under a condition where its surface is covered with a liquid is used for the evaluation method according to the present invention. As long as a surface of the object to be evaluated for wetting characteristic is covered with a liquid, other portions may or may not be covered with the liquid. For example, only a surface of a sheet-like object at the side for wetting characteristic evaluation may be covered with a liquid, or both of the surfaces may be covered with the liquid. Note that in the present invention, "a surface (of an object)" may mean that a surface for which wetting characteristic is evaluated, and in other words, a surface at which a gas is jetted unless otherwise stated. As long as wetting characteristic evaluation can be performed at a desired portion of an object, the entire surface may be covered with a liquid, or a portion of the surface may be covered with the liquid. For example, the object may be covered with a liquid on 50% or more, 80% or more, 90% or more, 95% or more, 99% or more, or 100% of its surface. The object may have a surface inherently covered with a liquid, or may have a surface intentionally covered with a liquid for use in the evaluation method according to the present invention. The object may be immersed into a liquid. It may be suspended or may be sunk on the bottom in a liquid. It may or may not be fixed in a liquid. For example, the object may have a surface covered with a liquid, and may be fixed to any member at its different portion. Specific examples of such an aspect include a cell sheet which is attached on a culture device (for example, a culture dish and a culture insert), and covered with a liquid culture medium. For example, a cell sheet formed on a culture device may be directly used for the evaluation method according to the present invention. Alternatively it may be used for the evaluation method according to the present invention after a culture medium is replaced with any liquid or after it is detached from the culture device and immersed in any liquid. Further, in addition to a cell sheet, if a surface of a culture device involved in culturing which is covered with a culture medium actually used for culturing is subjected to the evaluation method according to the present invention, the wetting characteristic of the surface can be appropriately evaluated under the same conditions as in the actual culture (see Example 2).

There is no particular limitation for liquids, and any desired liquids may be used for which the wetting characteristic of an object is evaluated. Liquids include, for example, an aqueous medium. An aqueous medium may consists of water or may comprise another component(s). With regard to the above another component(s), only one component may be contained, or two or more components may be contained. Aqueous media include, for example, water, buffer solutions, and liquid culture media. For example, a liquid may be a liquid culture medium which will be used or has been used for cell culture of a cell sheet and the like.

A thickness of a liquid layer may or may not be uniform. A thickness of a liquid layer may be uniform over the entire surface of an object or may be uniform at a portion of the surface. A thickness of a liquid layer may be uniform, for example, at least in a region where a surface of an object is exposed by a gas jet. There is no particular limitation for a thickness of a liquid layer as long as a surface of an object is exposed by a gas jet, but it can be suitably selected depending on factors such as a type of the liquid, and the amount of a gas jet. A thickness of a liquid layer may be, for example. 0.5 mm to 5 mm, or specifically, 1 mm. A thickness of a liquid layer may fall in the range illustrated above over the entire surface of an object, or may fall in the ranges illustrated above at a portion of the surface. A thickness of a liquid layer may fall in the range illustrated above at least in a region where a surface of an object is exposed by a gas jet.

An object under a condition where it can hold a liquid may be used for the evaluation method according to the present invention. For example, an object under a condition where it is contained in an appropriate container together with a liquid may be used for the evaluation method according to the present invention. Containers include, for example, a cell culture dish. Further, for example, an object under a condition where the object itself holds a liquid as a container may also be used for the evaluation method according to the present invention. Specific examples of such an aspect include a case in which the wetting characteristic of an inner surface (inner bottom surface) of a culture dish holding a liquid is evaluated. For example, an object positioned such that its surface is horizontal may be used for the evaluation method according to the present invention. An object positioned such that the entirety or a portion of its surface is horizontal may be used for the evaluation method according to the present invention. For example, an object positioned such that its surface is horizontal at least in a region where the surface is exposed by a gas jet may be used for the evaluation method according to the present invention.

The evaluation method according to the present invention comprises a step of jetting a gas at a surface of an object covered with a liquid. This step is also referred to as "the gas jetting step." A liquid covering a surface of an object is temporarily removed by a gas jet, and the surface of the object is exposed at the bottom of a liquid layer. A range in which a liquid is removed, i.e., a hole-like structure formed at the liquid layer is also referred to as a "liquid exclusion region." The liquid exclusion region usually has a hole-like structure having a circular cross-section.

There is no particular limitation for a gas, but it can be suitably selected depending on factors such as a material of the object. A gas having no negative effect on the object is preferably selected for use. Gases include air and inert gases. Specific examples of inert gases include nitrogen and argon. The gas may be used after sterilization, or may be used without sterilization. One type of gas may be used alone, or two or more types of gases may be used in combination.

The amount of a gas jet may be suitably selected depending on factors such as a material of the object, a type of the liquid, and a thickness of the liquid layer. The amount of a gas jet may be such that the diameter of the liquid exclusion region upon jetting a gas is, for example, 2 mm to 10 mm, specifically 5 mm. Further, the amount of a gas jet may be such that a force applied to the object is, for example, 1 mN to 20 mN, specifically 5 mN. Moreover, the amount of a gas jet may be such that a pressure applied to the object is, for example, 2 kPa to 50 kPa, specifically 14 kPa.

A gas is jetted from above the liquid layer. A gas may be jetted from vertically above the liquid layer, or may be jetted from obliquely above the liquid layer. A gas is preferably jetted from vertically above the liquid layer. In a case where a gas is jetted from obliquely above the liquid layer, there is no particular limitation for the angle as long as a liquid exclusion region having a measurable dimension is formed, but it is preferably close to perpendicular to a surface of the liquid layer.

Gas jetting may be performed only once, or twice or more. Gas jetting may be performed continuously or intermittently. In a case where gas jetting is performed twice or more, conditions such as types of the gas, the amount and duration of jetting may or may not be the same for each jetting. Further, in a case where gas jetting is performed continuously, conditions such as types of the gas and the amount of jetting may or may not be constant throughout the course of jetting. The duration of gas jetting may be, for example, 0.1 second to 5 seconds, and specifically 1 second. Gas jetting may usually be performed continuously under constant conditions.

There is no particular limitation for a method of jetting a gas as long as a liquid exclusion region having a measurable dimension is formed. Gas jetting can be performed using an appropriate gas jetting unit. For a gas jetting unit, a gas jetting device and a gas feeder may be suitably used in combination. Gas jetting devices include a gas nozzle. Gas feeders include a compressor and a gas cylinder. A gas jetting device may be connected to a gas feeder through an appropriate gas flow line to allow a gas to be jetted from the gas jetting device. An inner diameter of a gas nozzle may be suitably selected depending on factors such as the amount of gas jetting. An inner diameter of a gas nozzle may be, for example, 10 μm to 100 μm, and specifically 50 μm. A gas jetting distance (a distance from a surface of a liquid layer to a gas jetting device) may be suitably selected depending on factors such as the amount of gas jetting. The gas jetting distance may be, for example. 0.5 mm to 5 mm, and specifically 1 mm.

A gas jet can be controlled by a suitable means for controlling a gas flow. For example, a gas jet can be controlled by suitably combining an electropneumatic regulator with an electromagnetic valve. Specific examples of an electropneumatic regulator include ITV2050-312CS-Q (SMC CORP., Japan). Specific examples of an electromagnetic valve include a solenoid valve VA01PSP23-1P (KURODA Pneumatics Ltd., Japan). A gas jet may be controlled automatically or manually. For example, a gas jet can be automatically controlled by controlling an electropneumatic regulator and an electromagnetic valve via a computer.

The evaluation method according to the present invention comprises a step of measuring a dimension of a liquid exclusion region after the completion of gas jetting. This step is also referred to as "the dimension measuring step." A "dimension of a liquid exclusion region" as used herein means a value which reflects the extent of liquid exclusion, and specifically may be a value which reflects the radius of a liquid exclusion region. Specific examples of a dimension include a radius, a diameter, a circumferential length, an area and a volume. For the dimension, only one value may be measured, or two or more values may be measured.

With regard to the dimension, in general, a dimension (the diameter and the like) of a surface of an object exposed at the bottom of a liquid exclusion region may be measured. Further, with regard to the dimension, a dimension (the diameter and the like) of a liquid exclusion region at a surface of a liquid layer or at any depth in the liquid layer. These values also reflect the extent of liquid exclusion.

There is no particular limitation for the timing of measuring a dimension as long as it is after the completion of gas jetting. "After the completion of gas jetting" may be, for example, 1 second to 10 seconds after the completion of gas jetting, and specifically 3 seconds after the completion of gas jetting. Note that "after the completion of gas jetting" means after the completion of a continuous gas jet when gas jetting is performed continuously, and means after the completion of the last gas jet when gas jetting is performed intermittently.

Measuring a dimension may be performed only once, or twice or more. "Measuring a dimension is performed twice or more" may refer to performing multiple measurements of a dimension of a single liquid exclusion region, or may refer to repeating a set of the formation of a liquid exclusion region by jetting a gas and a dimension measurement for multiple times, or may refer to a combination thereof. In a case where the above set are repeated for multiple times, a place to which a gas is jetted and a place at which a dimension is measured may or may not be the same for each time. In a case where gas jetting and a dimension measurement are performed at multiple places, the gas jetting and dimension measurement may or may not be performed simultaneously at each place.

There is no particular limitation for a method of measuring a dimension as long as a target dimension can be obtained in a non-contact fashion. Dimension measurements can be performed using an appropriate measurement device. For example, a liquid exclusion region can be photographed to obtain a dimension of the liquid exclusion region from the resulting photographed image. In other words, a measurement device may comprise, for example, an imaging unit for photographing a liquid exclusion region, and may further comprise a dimension acquiring unit for obtaining a dimension of the liquid exclusion region from the resulting photographed image.

There is no particular limitation for the imaging unit as long as it can capture an image from which a target dimension can be obtained. The photographed image may be obtained as a two-dimensional image or a three-dimensional image. The photographed image may be obtained as a video or a still image. The number of pixel and a frame rate of a photographed image can be suitably selected depending on types of measurements.

The imaging unit may detect light selected from, for example, visible light, infrared light and ultraviolet light, and may preferably detect visible light. As the imaging unit, for example, an appropriate digital camera may be used. In a case where a three-dimensional image is captured, for example, a stereoscopic camera system may be assembled with appropriate digital cameras for use as an imaging unit, or an appropriate 3D scanner may be used. The digital camera may be a CCD camera or a CMOS camera. The digital camera may be a video camera or a still camera. Specific examples of a CMOS digital video camera include HDR-SR1 (Sony Corporation, Japan).

There is no particular limitation for a dimension acquiring unit as long as a dimension of a liquid exclusion region can be obtained from a photographed image. For example, a dimension of a liquid exclusion region in a photographed image can be obtained by identifying a region corresponding to the liquid exclusion region in the photographed image and measuring the identified region. A dimension may be obtained manually or automatically. In a case where a dimension is obtained automatically, a target dimension can be obtained, for example, by automatically identifying a region corresponding to the liquid exclusion region in a photographed image and measuring the identified region using an appropriate image-processing software.

The dimension of a liquid exclusion region in a photographed image obtained in this way may be used for wetting characteristic evaluation directly or after appropriately processed. For example, correlation data between an actual dimension of a liquid removed region and a dimension of the liquid removed region in a photographed image may be used to calculate the actual dimension of the liquid removed region from the dimension of the liquid removed region in the photographed image. Further, for example, given photographing conditions such as object distances and photographing angles, a dimension of a liquid exclusion region in a photographed image may be normalized. Dimensions can be compared even between samples having different photographing conditions such as object distances and photographing angles by using the standardized data. In other words, a measurement device may include, for example, a calculation unit for computing an actual dimension of a liquid exclusion region from a dimension of the liquid exclusion region in a photographed image, or a processing unit for standardizing the dimension of the liquid exclusion region in the photographed image.

A "dimension of a liquid exclusion region" measured in the evaluation method according to the present invention, and used as an index of wetting characteristic evaluation may be an actual dimension of the liquid exclusion region, or may be data reflecting the actual dimension of the liquid removed region which can be compared between samples. In other words, for "measuring a dimension of a liquid exclusion region," if data reflecting an actual dimension of a liquid exclusion region which can be compared between samples are available, the actual dimension of the liquid exclusion region needs not be computed. "Data reflecting an actual dimension of a liquid exclusion region" include a dimension of the liquid exclusion region in a photographed image (for example, the number of pixels corresponding to a diameter) and data obtained by subjecting the dimension of the liquid exclusion region in the photography image to a processing such as standardization. Data of "a dimension of a liquid exclusion region" obtained in the measurement step may be called "measured values."

There is no particular limitation for a direction of a dimension measurement as long as a target dimension can be obtained. For example, the measurement can be performed from above the liquid layer. The measurement may be performed from vertically above the liquid layer, or may be performed from obliquely above the liquid layer. Further, in a case where an element involved in an implementation of the evaluation method according to the present invention has sufficient transparency for a measurement device, a measurement may be performed through the element. Elements involved in an implementation of the evaluation method according to the present invention may include, for example, an object, a liquid, a container and a measurement system. A "container" here refers to a member in which an object and liquid are contained. However, in a case where an object itself holds a liquid as a container, the "container" here may mean the object itself. For example, in a case the liquid layer and the container have sufficient transparency for a measurement device, a measurement may be performed from the transverse direction of the liquid layer. Further, for example, in a case where the object and the container have sufficient transparency for a measurement device, a measurement may be performed from below the object. Further, for example, in a case where the container is placed on the stage, and where a measurement is performed through the stage from below the stage, the stage itself, as well as the object and the container, has sufficient transparency for a measurement device. "Sufficient transparency for a measurement device" refers to being transparent for a measurement device selected to the extent enough to allow a dimension to be measured by the measurement device. Specifically, in a case where, for example, an imaging unit for detecting visible light is used as a measurement device, "sufficient transparency for a measurement device" refers to a property in which visible light penetrates through to the extent enough to obtain a photographed image from which a target dimension can be obtained.

In the evaluation method according to the present invention, an implementation means at each step and a sample to be evaluated (an object, a liquid, or a container containing thereof) may be physically moved if desired. For example, in a case where both gas jetting and dimension measurements are performed from vertically above, a gas jetting unit and a measurement unit may be physically moved, or a sample may be physically moved so that a liquid exclusion region is positioned right under the measurement unit after the completion of gas jetting.

The evaluation method according to the present invention comprises a step of evaluating the wetting characteristic of an object using a measured dimension of a liquid exclusion region as an index. This step is also called a "wetting characteristic evaluation step." "Using a measured value of a dimension as an index" means that the measured value of a dimension is directly or indirectly involved in the evaluation.

For example, the evaluation may be performed based on the measured value of a dimension itself. In this case, the wetting characteristic of an object can be evaluated to be higher when a measured value is smaller.

Further, for example, the evaluation may be performed based on changes in measured values of dimensions in a predetermined period of time. Examples of a predetermined period of time include a period from during gas jetting to a predetermined time point after the completion of gas jetting. A "predetermined time point" may be, for example, a time point of 0 to 10 seconds after the completion of gas jetting. Further, examples of a predetermined period of time include a period from a first time point after the completion of gas jetting to a second time point after the completion of a gas jetting. The "first time point" may be, for example, a time point of 0 to 0.5 seconds after the completion of gas jetting and the "second time point" may be, for example, a time point of 1 to 10 seconds after the completion of gas jetting. Examples of changes in measured values include differences between measured values and a rate of change in measured values. The wetting characteristic of an object can be evaluated to be higher when changes in measured values are larger.

Further, in a case where two or more measurements are performed, the evaluation may be performed considering all two or more measured values together. For example, the evaluation may be performed using, for example, the average value, the median value, the minimum value or the maximum value of two or more measured values as an index.

The evaluation may be performed manually or automatically. In a case where the evaluation is performed automatically, a degree of wetting characteristic can be automatically calculated, for example, based on correlation data between predetermined measured values of dimensions and wetting characteristic using suitable analysis software.

The wetting characteristic of an object can be evaluated as described above. Note that "evaluating wetting characteristic" includes not only evaluating wetting characteristic itself but also evaluating properties related to wetting characteristic.

For example, for a cell sheet, higher wetting characteristic may be correlated with better transplant compatibility of a cell sheet. In this case, "evaluating wetting characteristic" may correspond to evaluating transplant compatibility of a cell sheet. In other words, one aspect of the evaluation method according to the present invention may be a method of evaluating transplant compatibility of a cell sheet. For example, the evaluation method according to the present invention can be used to evaluate the wetting characteristic (transplant compatibility) of a cell sheet, and to select a cell sheet having high wetting characteristic (transplant compatibility) for use in transplantation.

Further, the wetting characteristic of a cell sheet can reflect a mucosal condition on a surface of a cell sheet. For example, a higher wetting characteristic of a cell sheet may correlate with more mucin (for example, MUC4 protein and the like) present on the surface of the cell sheet. In this case, "evaluating wetting characteristic" may correspond to evaluating a mucosal condition (for example, the abundance of mucin) on a surface of cell sheet. In other words, one aspect of the evaluation method according to the present invention may be a method of evaluating a mucosal condition (for example, the abundance of mucin) on a surface of a cell sheet. Evaluating a mucosal condition is useful for drug screening and drug efficiency evaluation. For example, the efficiency of a drug can be determined by exposing a cell sheet to the drug in vitro, and evaluating its mucosal condition.

<2> Manufacturing Method According to Present Invention

The manufacturing method according to the present invention is a method of manufacturing an object, comprising the step of evaluating the wetting characteristic of the object by the evaluation method according to the present invention. The object can be manufactured using a conventional material and method for manufacturing the object except that wetting characteristic is evaluated by the evaluation method according to the present invention. For example, for a method of manufacturing a cell sheet, known methods can be referred (D. Murayama, et al., *Biomaterials*, Vol. 27, pp. 5518-5523, 2006.; Japanese Patent Laid-Open No. 2011-224334, WO2011/016423 and the like). Wetting characteristic evaluation may be performed at any time during the steps of manufacturing an object, but in general, is preferably performed after the completion of manufacturing the object. Among the objects manufactured, those having a desired wetting characteristic can be selected for use, depending on factors such as intended uses.

<3> System According to Present Invention

The system according to the present invention is intended for evaluating the wetting characteristic of an object. The evaluation method according to the present invention can be performed, for example, using the system according to the present invention.

The system according to the present invention comprises a means for jetting a gas onto a surface of an object covered with a liquid. For such a means, gas jetting units as described above can be used. A liquid covering a surface of an object is temporarily removed by jetting a gas, and the surface of the object is exposed at the bottom of a liquid layer. A gas jetting unit may be used, for example, according to the implementation conditions in the gas jetting step as described above.

The system according to the present invention comprises a means for measuring a dimension of a liquid exclusion region. For such a means, measurement devices as described above may be used. A measurement device may include an imaging unit for photographing a liquid exclusion region. A measurement device may further include a dimension acquiring unit to obtain a dimension of a liquid exclusion region from a photographed image obtained. The measurement device may further include, for example a calculation unit for computing an actual dimension of a liquid exclusion region from a dimension of the liquid exclusion region in a photographed image, and a processing unit for standardizing the dimension of the liquid exclusion region in the photographed image. The measurement device may be used, for example, according to the implementation conditions in the gas jetting step as described above.

The system according to the present invention may comprise an evaluation device for evaluating the wetting characteristic of an object by using a measured dimension of a liquid exclusion region as an index. The evaluation device may use, for example, a suitable analysis software which computes a degree of wetting characteristic from a measured value based on the correlation data between pre-determined measured values of dimensions and wetting characteristic. The evaluation device may be used, for example, according to the implementation conditions in the wetting characteristic evaluation step as described above.

The system according to the present invention may comprise an illumination device for illuminating a liquid exclusion region when photographing. For the illumination device, for example, a suitable illuminator may be used. Illuminators include, for example, an incandescent lamp, a fluorescent lamp and a light emitting diode.

The system according to the present invention may comprise a holding device for holding an object and liquid.

The holding device may be, for example, a holder which directly holds an object and liquid. In other words, in this case, a holder serves as a container for an object and liquid. A shape of the holder can be suitably selected depending on factors such as a shape of the object and a volume of the liquid. The holder may be, for example, a member having a concave portion for containing an object and liquid.

The holding device may be, for example, a holder which indirectly holds an object and liquid by holding a container containing the object and liquid. However, in a case where an object itself holds a liquid as a container, the "container" here may mean the object itself. A shape of the holder can be suitably selected depending on factors such as a shape of the container. The holder may be, for example, a member having a scaffold on which the container is placed, or a member having a clamp for holding and gripping the container.

In a case where a component of the system such as a holding device interferes with measurements, the system according to the present invention is configured so that the component have sufficient transparency for a measurement device.

Any components of the system according to the present invention may be fixed to the system or movably configured. For example, a holder may be movable, or a gas jetting unit and an imaging unit may be movable. The system according to the present invention may comprise a position adjuster for adjusting the position of a component.

For any components of the system according to the present invention, only one may be provided, or two or more may be provide for each. For example, the system according to the present invention may comprise two or more gas jetting units, and may comprise two or more imaging units.

One embodiment of the system according to the present invention is a measurement system (FIG. 3) used in Examples described below.

<4> Program According to Present Invention

The program according to the present invention allows a computer to perform each step of the evaluation method according to the present invention.

In other words, one aspect of the program according to the present invention allows a computer to perform following steps (1) to (3):

(1) a step of removing a liquid by jetting a gas at a surface of an object covered with the liquid, (2) a step of measuring a dimension of a region where the liquid is removed after the gas jetting, and (3) a step of evaluating the wetting characteristic of the object using the measured dimension as an index.

The step (2) may comprise a step of photographing the liquid exclusion region. The step (2) may further comprise a step of obtaining the dimension of the liquid exclusion region from the resulting photographed image. The step (2) may further comprise, for example, a step of computing an actual dimension of the liquid exclusion region from the dimension of the liquid exclusion region in the photographed image and a step of standardizing the dimension of the liquid exclusion region in the photographed image.

The program according to the present invention may be recorded and provided in a computer readable recording medium. The term "computer readable recording medium" as used herein refers to that in which information such as data and programs are stored by electrical, magnetic, optical, mechanical, chemical mechanisms or the like, and in addition, from which the information stored therein can be retrieved via a computer. Such recording media include, for example a Floppy Disk®, a magneto-optical disk, CD-ROM, CD-R/W, DVD-ROM, DVD-R/W, DVD-RAM, DAT, an 8 mm tape, a memory card, a hard disk, ROM (read only memory), SSD and the like. The program according to the present invention may be recorded as a program which allows a computer to perform each step only once, or may be recorded in separate programs for each, or in separate programs in any combinations.

EXAMPLES

Although the present invention will be described in more detail with reference to the following Examples, these should not, in any way, be construed as intended to limit the present invention.

Example 1: Wetting Characteristic Evaluation for Cell Sheet

In this Example, wetting characteristic evaluation was performed by using three cell sheets as samples which were cultured under different conditions.

<1> Principle of Measurements

A possible principle of wetting characteristic measurements is described below, but the present invention is not intended to be bound by the following principle.

Figure 1:
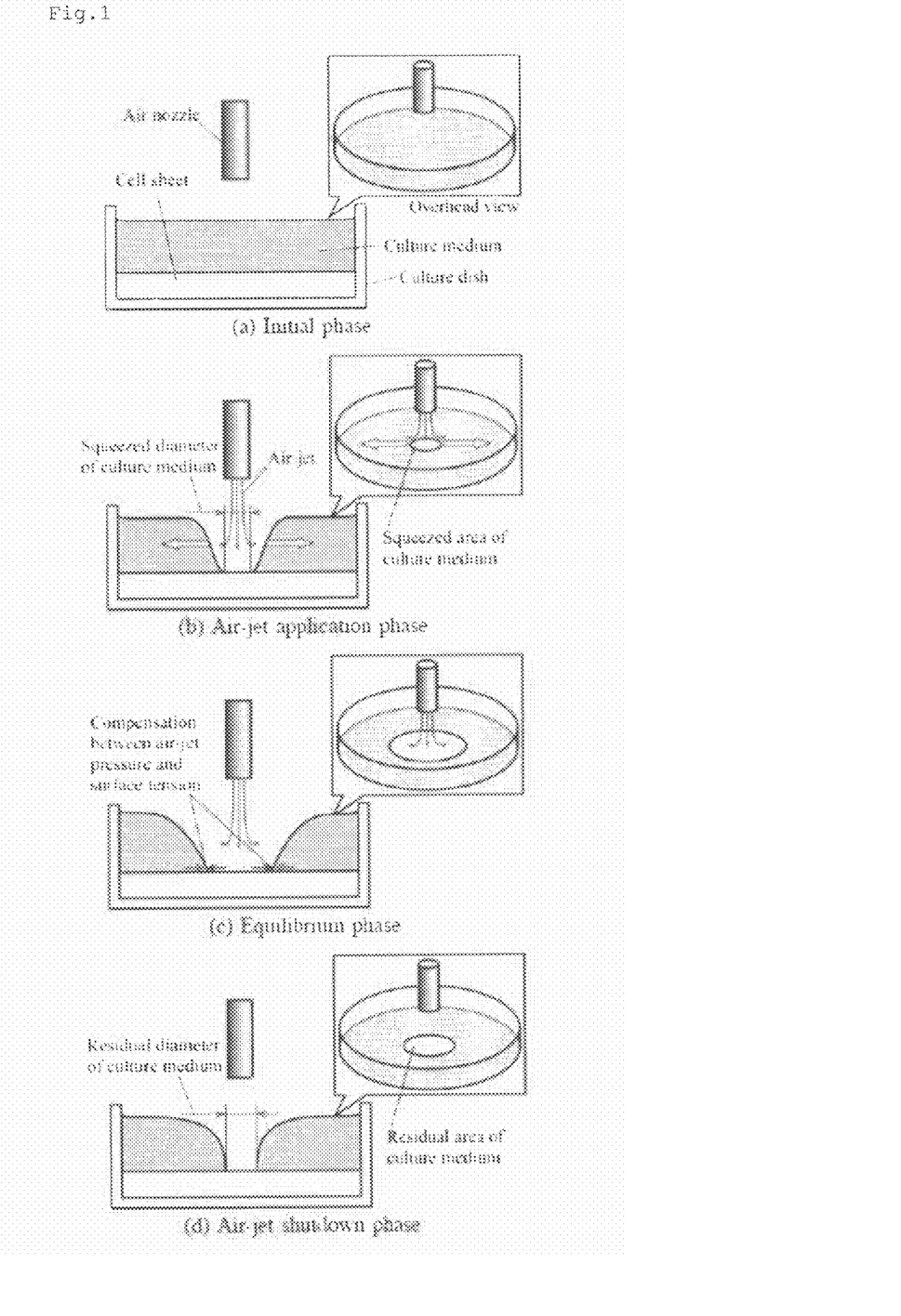
FIG. 1 shows the principle of wetting characteristic evaluation of a cell sheet.
Figure 2:
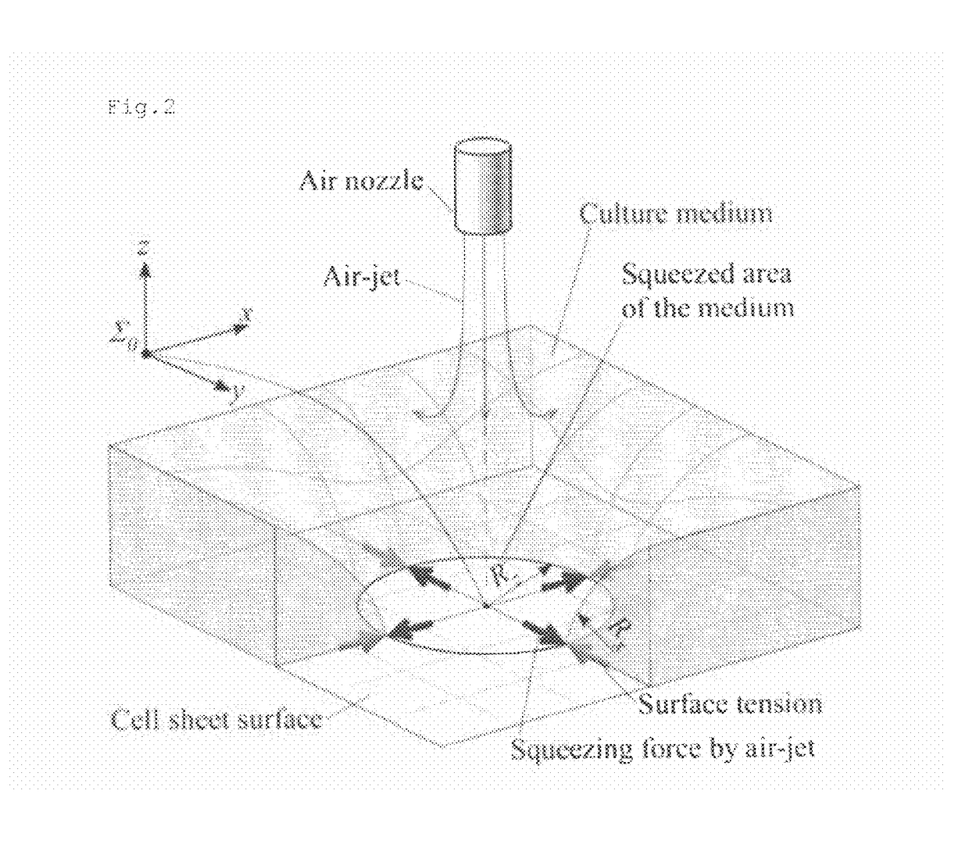
FIG. 2 shows a schematic view of the contact between a culture medium and a cell sheet when an air jet is applied.

The outline of measurement procedures used in this Example is shown in FIG. 1. First, a cell sheet in a culture dish is fixed under an air nozzle (FIG. 1 (a)). Then, an air jet (air jet flow) is applied from the air nozzle perpendicularly to the cell sheet to temporarily remove a liquid medium covering a surface of the cell sheet such that the surface of the cell sheet is exposed (FIGS. 1 (b) and (c)). Subsequently, when the air jet is stopped, the liquid medium removed returns toward the center (FIG. 1 (d)).

In equilibrium (FIG. 1 (c)), the squeezing force due to the pressure from the air jet will be in balance with the surface force exerted between the liquid medium and the surface of the cell sheet. Therefore, a region where the liquid medium is removed (squeezed area) depends on the wetting characteristic on the surface of the cell sheet. Specifically, the squeezing force $P_s$ due to the pressure from the air jet is represented by the following equation (1) from the Young-Laplace's equation.

$$p_s = \gamma\left(\frac{1}{R_x} + \frac{1}{R_z}\right) \quad (1)$$

wherein γ represents the surface tension of a liquid medium, $R_x$ represents a radius of curvature of a surface of the liquid medium at a contact point between the medium and a cell sheet, $R_z$ represents a radius of curvature of the squeezed area of a medium on the surface of the cell sheet, respectively. In a case where the directions of curvature for $R_x$ and $R_z$ are mutually opposite, i.e., the surface of the medium forms a portion of a parabolic hyperboloid at the contact point between the medium and the cell sheet, the surface tension arises inward and outward against the squeezed area due to the curvature of $R_x$ and $R_z$, respectively. A larger value of $R_x$ means higher wetting characteristic since the contact angle between the medium and the cell sheet becomes smaller. Solving the equation (1) in terms of $R_z$ will give the following equation (2).

$$R_z = \frac{\gamma R_x}{p_s R_x - \gamma} \quad (2)$$

In other words, in a case where γ and $P_s$ are constant, $R_z$ is a function of $R_x$ which reflects wetting characteristic. The wetting characteristic of a cell sheet can be estimated by measuring a radius of curvature of the squeezed area of a medium.

<2> Measurement System

Figure 3:
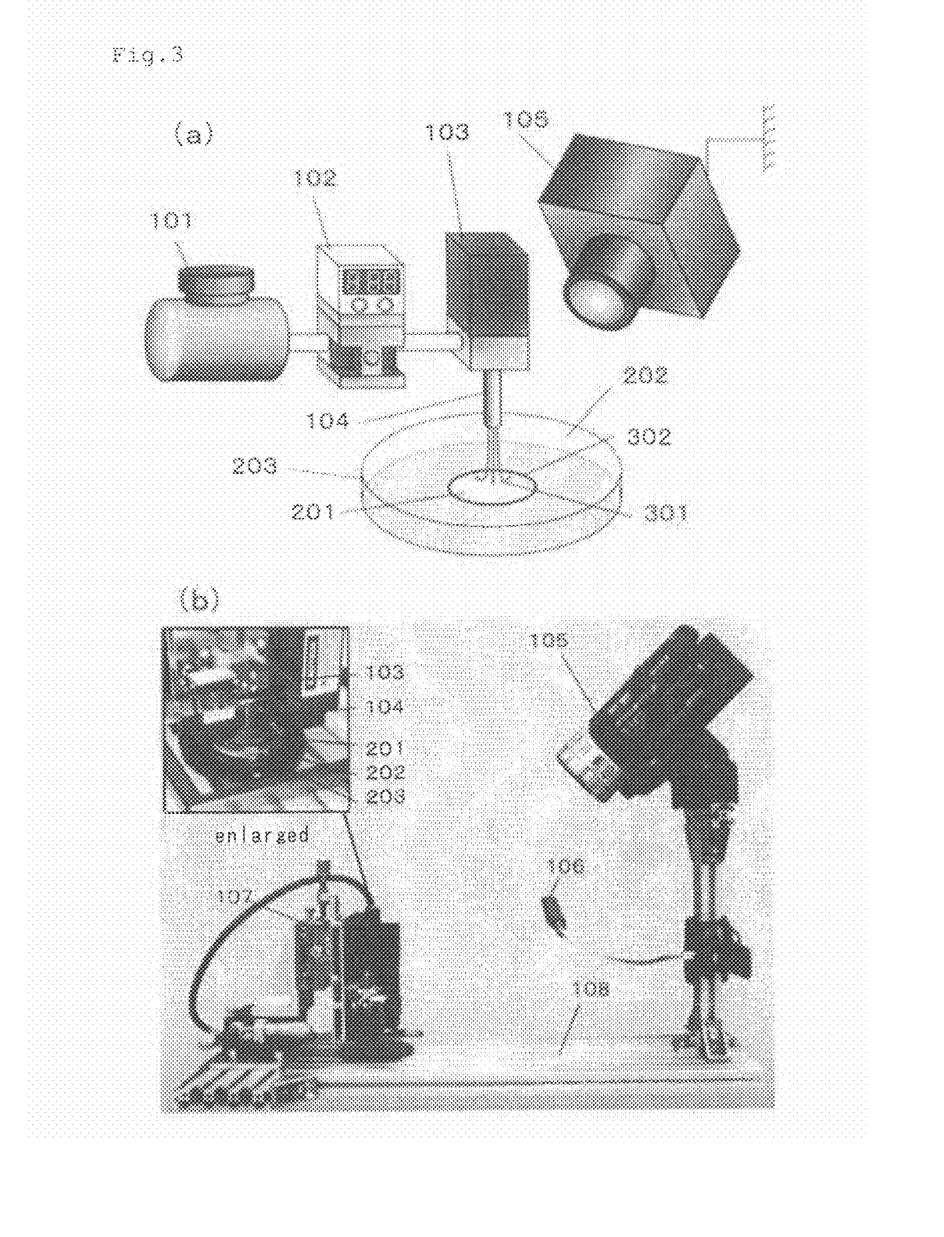
FIG. 3 shows a measurement system used in Example 1. (a) a schematic view of the system configuration and (b) a photograph.

FIG. 3 (a) and FIG. 3 (b) show a schematics diagram of the measurement system used in this Example and its picture, respectively. Air was supplied with an air compressor 101, and a flow rate of air was controlled using a high-speed solenoid valve 103 (VA01PSP23-1P, KURODA Pneumatics LTD., Japan) with a maximum switching frequency of 333 Hz and an electropneumatic regulator 102 (ITV2050-312 CS-Q, SMC Corporation, Japan) to jet an air jet 301 through an air nozzle 104 having an inner diameter of 0.2 mm. The solenoid valve 103 and the regulator 102 were controlled by a laptop computer (ThinkPad X61, Lenovo Japan, Japan) through an analog input/output interface module (CSI-360112, Interface Corporation, Japan). A surface of a cell sheet was observed using a digital video camera 105 (HDR-SR1, Sony Corporation, Japan) with a frame rate of 30 Hz. An air jet applying units 101 to 104 and the video camera 105 were firmly fixed to a base 108 of the measurement system.

<3> Preparation of Cell Sheets

Three cell sheets were prepared in accordance with the following procedures for wetting characteristic comparison. Oral mucosa epithelial cells of a rat were inoculated on a temperature responsive cell culture insert at an initial cell density of $5 \times 10^4$ cells/cm$^2$, and cultured in a cell culture dish containing a medium for 7 to 14 days under 5% $CO_2$ atmosphere at 37° C. to obtain layered cell sheets. The detailed culture conditions are according to the previous report (D. Murayama, et al., Biomaterials, Vol. 27, pp. 5518-5523, 2006). Keratinocyte culture media (KCM) described in the followings (a) to (c) were each used for culture.

(a) Control: normal KCM
(b) Cyto D (+): KCM containing Cytochalasin D (Cyto D)
(c) FBS (−): KCM containing no fetal bovine serum (FBS)

Cyto D is a polymerization inhibitor for actin fiber. The normal KCM contains FBS, but not Cyto D.

<4> Wetting Characteristic Measurements

After culturing, each cell sheet was detached from the insert in accordance with the conventional method, and transferred to a cell culture dish (cat. no. 353001, Becton, Dickinson and Company, US) containing 1.2 mL of the control medium (normal KCM), which was subjected to the wetting characteristic measurement.

An air jet was applied to a surface of each cell sheet for 1 second (from t=0.5 s to t=1.5 s). The amount of applied air jet was controlled so that the force (F) to be applied was 0.47 mN, 0.75 mN and 1.15 mN.

Figure 4:
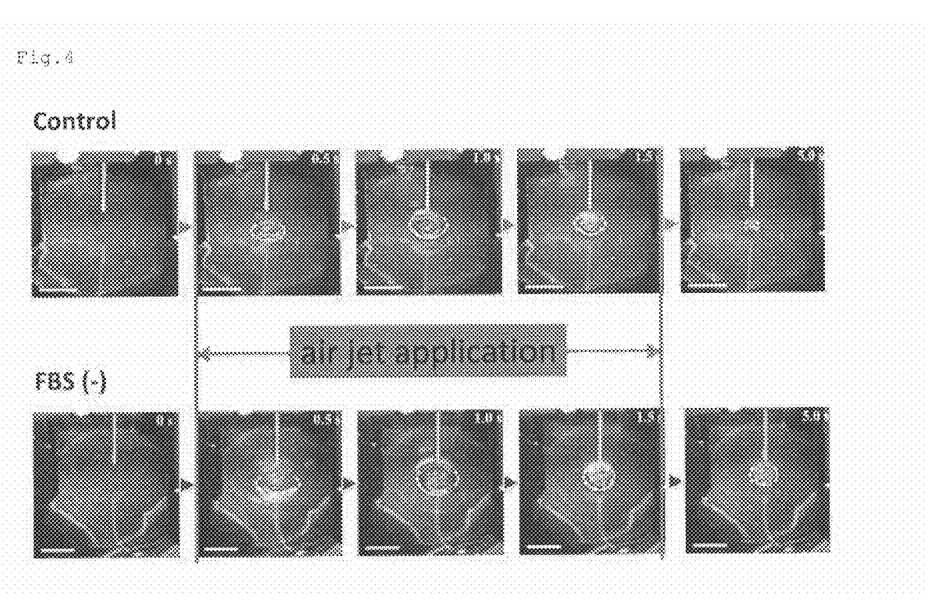
FIG. 4 shows photographs illustrating the appearances of cell sheets and culture media.

FIG. 4 shows changes in the appearance of the control and FBS (−) when F=1.15 mN. The areas of the squeezed area of a medium were almost the same for all cell sheets during air jet application (some are shown in FIG. 4). Further, after the completion of air jet application, the medium immediately covered the squeezed area again for the control while the squeezed area of a medium remained for a while for Cyto D (+) and FBS (−) (some are shown in FIG. 4). Note that the squeezed area of a medium remained after the completion of air jet application was larger for FBS (−) than for Cyto D (+).

Figure 5:
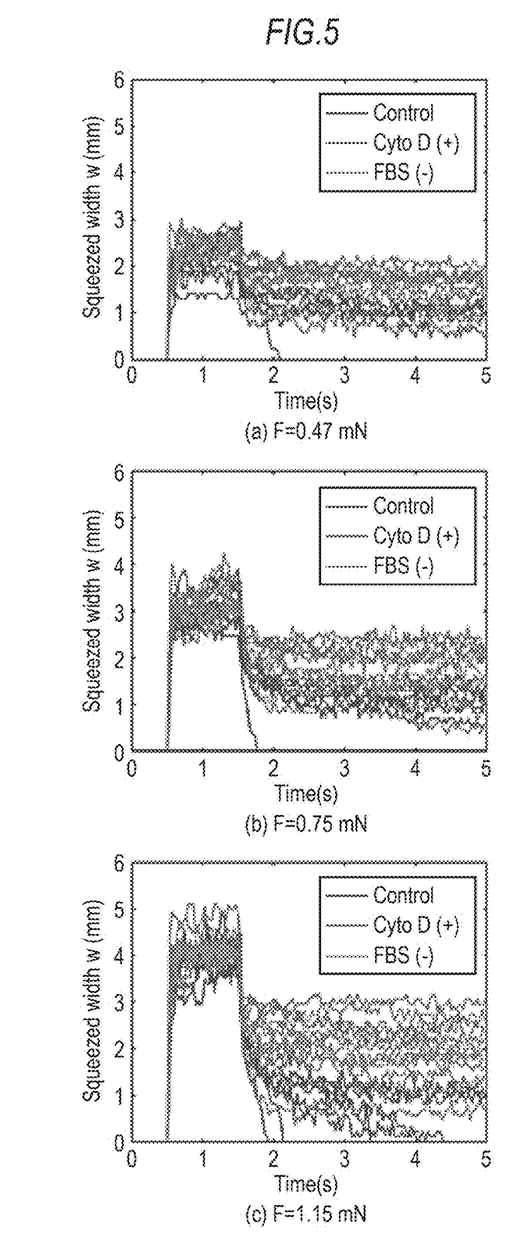
FIG. 5 shows a time-dependent width w of the squeezed area of a medium.
Figure 6:
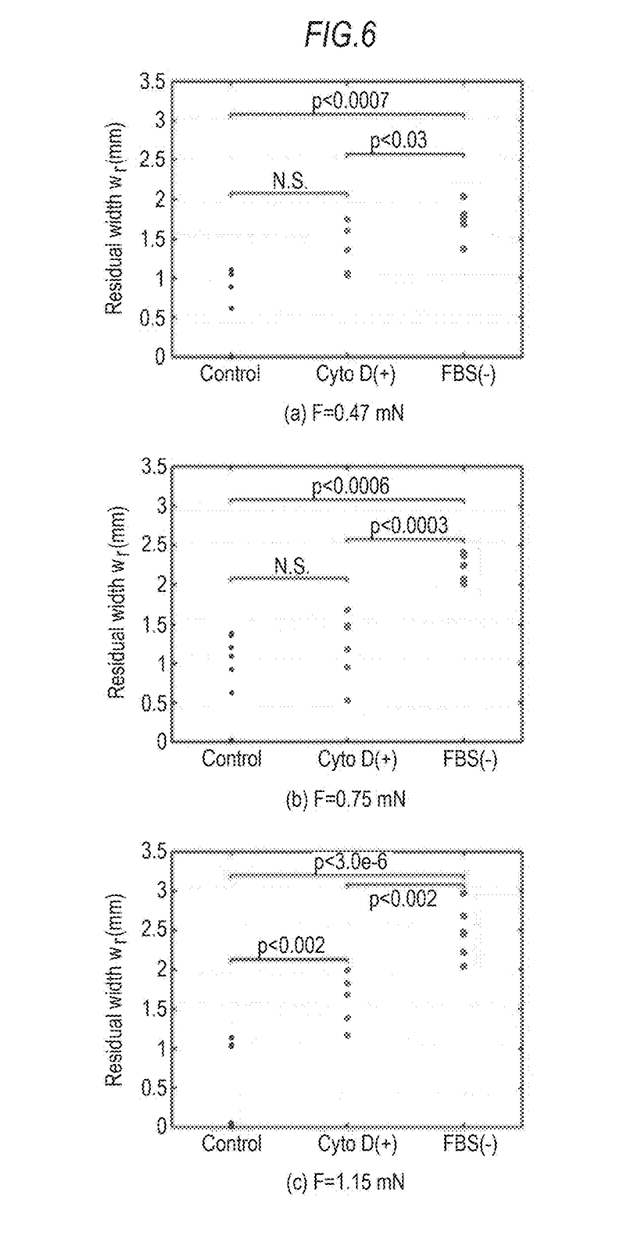
FIG. 6 shows a residual width $w_r$ of the squeezed area of a medium after the completion of air jet application.
Figure 7:
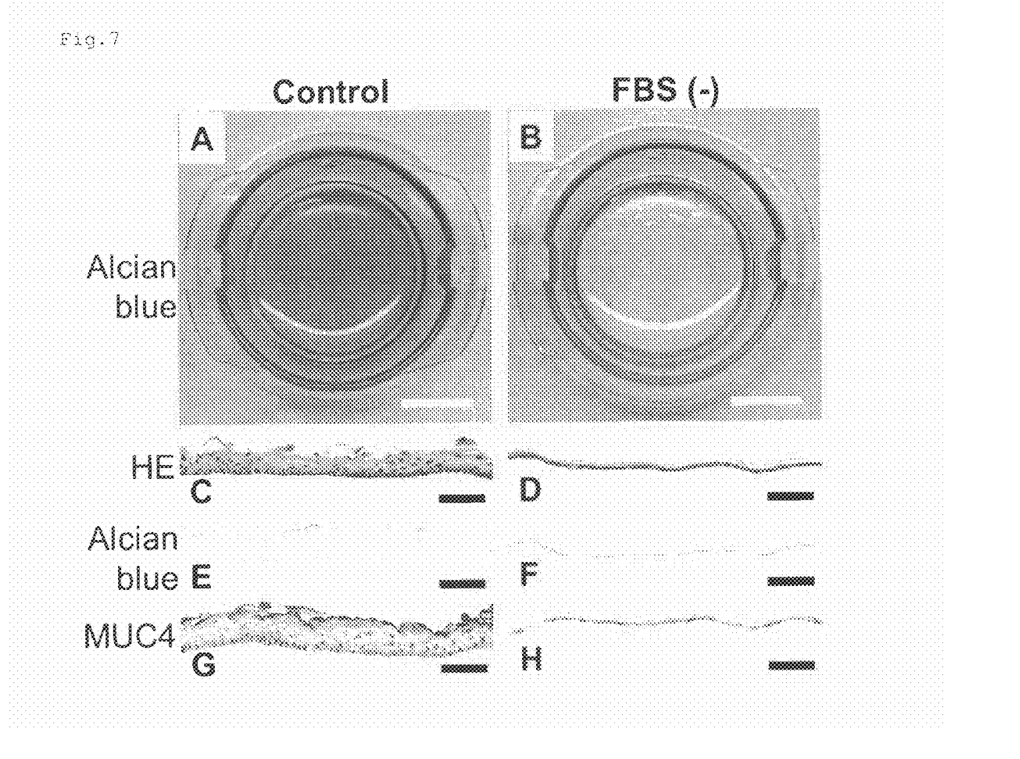
FIG. 7 shows photographs illustrating results from biochemical analysis of cell sheets.

FIG. 5 shows changes in a width w of the squeezed area of a medium under each condition. Further, FIG. 6 shows the average values of the width w of the squeezed area of a medium from t=4 s to t=5 s (from 2.5 s to 3.5 s after the completion of air jet application) under each condition as a residual width $w_r$ of the squeezed area of a medium after the completion of air jet application.

When F=0.47 mN and F=0.75 mN, significant difference in $w_r$ was observed between the control and Cyto D (+) and between Cyto D (+) and FBS (−) (P<0.05; FIG. 6). Further, when F=1.15 mN, significant difference in $w_r$ was observed between the control and Cyto D (+), between the control and FBS (−) and between Cyto D (+) and FBS (−) (P<0.05; FIG. 6).

As described above, the differences in wetting characteristic of cell sheets were distinguished by a degree of return of the medium after the completion of air jet application. Specifically, the residual width $w_r$ of the squeezed area of a medium after the completion of air jet application was larger in the following order: FBS (−)>Cyto D (+)>the control. In other words, the wetting characteristic of a cell sheet appeared to be larger in the following order: the control>Cyto D (+)>FBS (−).

Note that an increased amount of an applied air jet can be preferred to obtain a better result as long as a cell sheet is not damaged since significant difference was observed for each pair of the cell sheets when F=1.15 mN.

<5> Biochemical Analysis

Next, the control cell sheet which was evaluated to have large wetting characteristic and the FBS (−) cell sheet which was evaluated to have small wetting characteristic were biochemically analyzed.

Possible causes for the difference in wetting characteristic may include, for example, different production levels of specific proteins in cells, and different surface roughness of cell sheets. Mucin is known as a protein which is responsible for wetting characteristic on a surface of a cell. Accordingly, the DNA microarray analysis was performed and the expression levels of the mucin genes were compared. The results are shown in Table 1. They revealed that the control cell sheet expressed the MUC4 gene 60 folds or more as compared with the FBS (−) cell sheet. Therefore, MUC4 was assumed to be responsible for the difference in wetting characteristic observed in this Example.

TABLE 1

| Genes | Expression (Control/FBS(−)) | p values |
|---|---|---|
| MUC1 | 2.51 | 0.059 |
| MUC3 | 0.997 | 1.00 |
| MUC4 | 63.2 | 0.0062 |
| MUC5ac | 2.04 | 0.38 |
| MUC10 | 0.436 | 0.43 |
| MUC13 | 1.25 | 0.86 |

Further, hematoxylin-eosin staining (HE staining), Alcian blue staining and MUC4 immunostaining were performed. The results are shown in Table 7. From the Alcian blue staining, the localization of mucosal polysaccharides on a surface layer of a cell sheet was observed specifically for the control cell sheet. Further, form the MUC4 immunostaining, the localization of MUC4 on a surface layer of a cell sheet was observed specifically for the control cell sheet.

<6> Implantation of Cell Sheets

Figure 8:
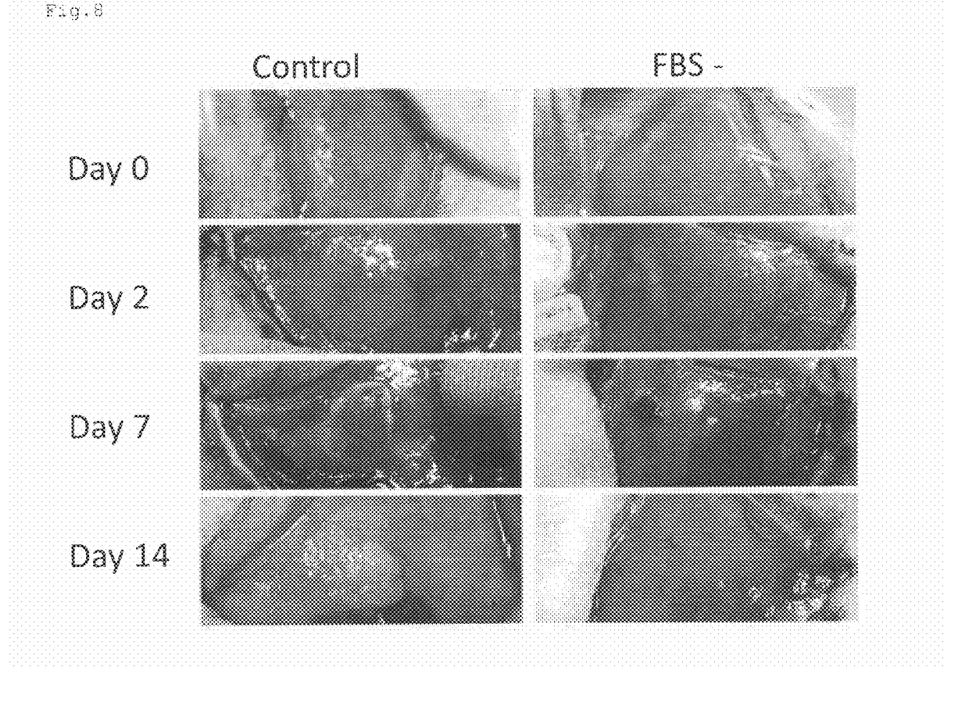
FIG. 8 shows photographs illustrating results from implantation of cell sheets.

Next, the control cell sheet which was evaluated to have large wetting characteristic and the FBS (−) cell sheet which was evaluated to have small wetting characteristic were allotransplanted into rats. FIG. 8 shows photographs of transplanted regions at Day 0 to 14 after transplantation. As a result of transplantation, the FBS (−) cell sheet disappeared at the transplanted region while the control cell sheet remained in the transplanted region as a population of cells distinguishable from adjacent cells. Therefore, a cell sheet having large wetting characteristic can be useful in terms of regenerative medicine.

Example 2: Wetting Characteristic Evaluation for Culture Dishes

In this Example, wetting characteristic evaluation was performed using culture dishes as samples.

Figure 9:
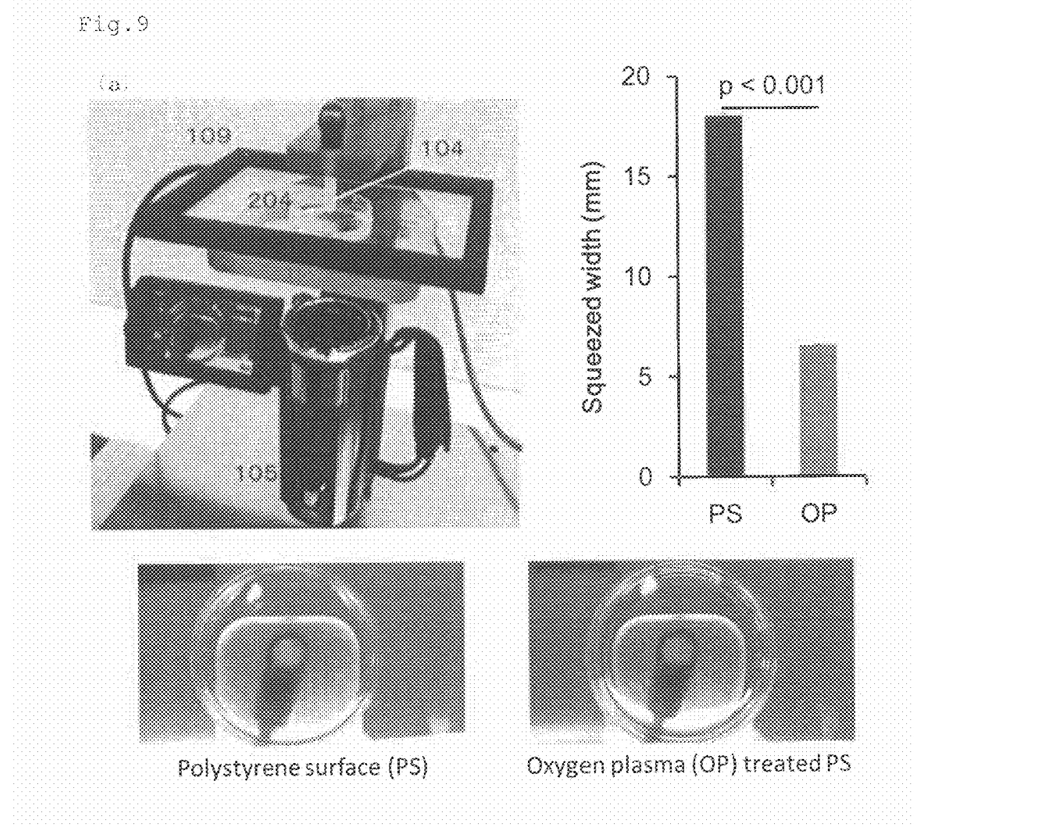
FIG. 9 shows wetting characteristic evaluation after surface treatment of culture dishes. (a) a photograph showing a measurement system used in Example 2, (b) a graph showing a residual width of the squeezed area of a medium after the completion of air jet application, (c) a photograph showing the appearance of a culture dish without oxygen plasma treatment (PS), (d) a photograph showing the appearance of a culture dish with oxygen plasma treatment (OP).

A polystyrene culture dish having a surface coated with a temperature responsive polymer was surface-treated with oxygen plasma. The control medium (normal KCM) was added to a culture dish without oxygen plasma treatment (PS) and a culture dish with oxygen plasma treatment (OP) for each to evaluate the wetting characteristic of an inner surface (inner bottom surface) in accordance with the same procedure as in Example 1 using the measurement system shown in FIG. 9 (a). The appearances of each culture dish are shown in FIGS. 9 (c) and (d). The results are shown in Table 9 (b). The residual width $w_r$ of the squeezed area of a medium after the completion of air jet application was smaller for the culture dish with oxygen plasma treatment (OP) as compared with the culture dish without oxygen plasma treatment (PS) ($P<0.001$; FIG. 9($b$)). In other words, wetting characteristic was assumed to be larger for the culture dish with oxygen plasma treatment (OP) as compared with the culture dish without oxygen plasma treatment (PS).

INDUSTRIAL APPLICABILITY

According to the present invention, the wetting characteristic of an object such as a cell sheet and a culture dish can be evaluated in a non-contact fashion.

DESCRIPTION OF REFERENCE NUMERALS

101: Air Compressor
102: Electropneumatic regulator
103: Solenoid valve
104: Air nozzle
105: Video camera
106: Illuminator
107: Position adjuster
108: Base
109: Glass plate with heater
201: Cell sheet
202: Liquid medium
203: Culture dish
204: Sample (culture dish)
301: Air jet
302: Squeezed area of medium

What is claimed is:

1. A method of evaluating a wetting characteristic of an object, the method comprising:
   (a) removing a liquid by jetting a gas at a surface of the object covered with the liquid, and
   (b) measuring a dimension of a region where the liquid is removed after the gas jetting, by photographing the region in which the liquid is removed, and obtaining the dimension of the region in which the liquid is removed from the photographed image,
   wherein the dimension of the region is at least one spatial dimension selected from the group consisting of a radius, a diameter, a circumferential length, an area, and a volume of the region.

2. The method according to claim 1, wherein the object is a sheet-shaped object.

3. The method according to claim 2, wherein the sheet-shaped object is a cell sheet.

4. The method according to claim 1, wherein the liquid is a culture medium.

5. The method according to claim 1, wherein the gas is air.

6. The method according to claim 1, wherein the object is a cell sheet, the gas is air, and the liquid is a culture medium.

7. The method according to claim 1, wherein the object is a culture dish, the gas is air, and the liquid is a culture medium.

8. The method according to claim 1, wherein a dimension of a surface of the region where the liquid is removed is measured.

* * * * *